(12) United States Patent
Borges

(10) Patent No.: US 8,883,681 B2
(45) Date of Patent: Nov. 11, 2014

(54) SUGARCANE HARVEST AID

(75) Inventor: Alan Borges, Sao Paulo State (BR)

(73) Assignee: FMC Corporation, Philadelphia, PA (US)

( * ) Notice: Subject to any disclaimer, the term of this patent is extended or adjusted under 35 U.S.C. 154(b) by 1827 days.

(21) Appl. No.: 11/568,393

(22) PCT Filed: Apr. 28, 2005

(86) PCT No.: PCT/US2005/014775
§ 371 (c)(1),
(2), (4) Date: Aug. 14, 2007

(87) PCT Pub. No.: WO2005/104791
PCT Pub. Date: Nov. 10, 2005

(65) Prior Publication Data
US 2008/0261813 A1    Oct. 23, 2008

Related U.S. Application Data

(60) Provisional application No. 60/565,884, filed on Apr. 28, 2004.

(51) Int. Cl.
| | |
|---|---|
| *A01N 57/00* | (2006.01) |
| *A01N 57/10* | (2006.01) |
| *A01N 43/653* | (2006.01) |
| *A01P 21/00* | (2006.01) |
| *A01N 43/54* | (2006.01) |
| *A01N 37/46* | (2006.01) |
| *A01N 41/06* | (2006.01) |
| *A01N 43/56* | (2006.01) |
| *A01N 37/48* | (2006.01) |
| *A01N 33/22* | (2006.01) |
| *A01N 39/04* | (2006.01) |
| *A01G 7/06* | (2006.01) |
| *A01N 43/58* | (2006.01) |
| *A01N 43/90* | (2006.01) |

(52) U.S. Cl.
CPC *A01G 7/06* (2013.01); *A01N 43/54* (2013.01); *A01N 37/46* (2013.01); *A01N 41/06* (2013.01); *A01N 43/56* (2013.01); *A01N 37/48* (2013.01); *A01N 33/22* (2013.01); *A01N 43/653* (2013.01); *A01N 39/04* (2013.01); *A01N 43/58* (2013.01); *A01N 43/90* (2013.01)
USPC ............................ 504/128; 504/127; 504/272

(58) Field of Classification Search
None
See application file for complete search history.

(56) References Cited

U.S. PATENT DOCUMENTS

| | | | | |
|---|---|---|---|---|
| 3,853,530 A | * | 12/1974 | Franz ............................ | 504/165 |
| 3,988,142 A | * | 10/1976 | Franz ............................ | 504/206 |
| 5,147,444 A | * | 9/1992 | Decor et al. .................. | 504/127 |
| 6,486,157 B1 | | 11/2002 | Lee | |
| 6,919,299 B2 | | 7/2005 | Hacker et al. | |
| 7,713,913 B2 | * | 5/2010 | Garcia et al. .................. | 504/128 |
| 2002/0183206 A1 | * | 12/2002 | Jimoh ............................ | 504/128 |
| 2003/0166469 A1 | * | 9/2003 | Bahr et al. .................... | 504/273 |

FOREIGN PATENT DOCUMENTS

GB    2313595 A * 12/1997

OTHER PUBLICATIONS

Dayan et al., "Selectivity and Mode of Action of Carfentrazone-ethyl, a Novel Phenyl Triazolinone Herbicide", Pestic. Sci. 1997, 51, pg. 65-73.*
Bennett et al., "Weeds in the Sunshine: Weed Management in Sugarcane", University of Florida Extension: Institute of Food and Agricultural Sciences, SS-AGR-09, 2002, p. 1-6.*
Purdue University Center for New Crops & Plant Products, "Sugar cane," <http://www.hort.purdue.edu/newcrop/crops../Sugar_cane.html>, last updated Nov. 7, 2013, p. 1-3.*
UCLA, "Sucrose on a Stick," Economic Botany, <http://www.botgard.ucla.edu/html/botanytextbooks/economicbotany/Saccharum/>, published Oct. 28, 2003, p. 1-2.*
Netafim, "Weed Management," <http://www.sugarcanecrops.com/agronomic_practices/weed_management/>, published Feb. 25, 2013, p. 1-3.*
Bayer—Laudis Herbicide Label, Copyright 2011.

* cited by examiner

*Primary Examiner* — Tracy Vivlemore
*Assistant Examiner* — Monica Shin
(74) *Attorney, Agent, or Firm* — FMC Corporation

(57) ABSTRACT

Protoporphyrinogen oxidase enzyme-inhibiting compounds are useful in compositions and methods for ripening sugarcane crops. Of particular interest is the use of carfentrazone ethyl and certain metabolites thereof for ripening sugarcane crops.

11 Claims, No Drawings

SUGARCANE HARVEST AID

This application claims the benefit of U.S. Provisional Application No. 60/565,884, filed Apr. 28, 2004.

FIELD OF THE INVENTION

The present invention relates to harvest aids for use in sugarcane production.

BACKGROUND OF THE INVENTION

Sugarcane is a crop of great importance within the agricultural sector and its cultivation is related to the production of sugar, industrial alcohol and fuel, rum and wax.

In abnormal weather conditions such as the green-house effect or the "El Niño" effect, the atmospheric temperature and moisture can often stay above normal and cause severe sugarcane yield losses, specifically from the lack of ripening. When the lack of ripening is from these natural causes, the use of chemical ripeners can help to solve the problem and mitigate the environmental conditions.

Chemical ripeners are also used when a sugarcane crop is in the middle or at the end of the crop season, and there are intentions to harvest before the natural period of ripening. Finally, chemical ripeners are also utilized when control of sugarcane blooming is desired.

Chemical ripeners preserve or even increase the yield of the sugarcane crop in the above-mentioned scenarios. Traditionally, glyphosate and trinexapac-ethyl have been used as chemical ripeners in sugarcane crops. Common problems with using these traditional chemical ripeners are reduced yield of return crops and high use rates. High use rates can adversely affect cost, handling issues and the environment.

SUMMARY OF THE INVENTION

It has now been found that the use of protoporphyrinogen oxidase enzyme-inhibiting (PPO-inhibiting) compounds as chemical ripeners provides additional benefits as compared to traditional chemical ripeners. These additional benefits include no effect on return crop yields, improved harvestability of the sugarcane crop by killing a wide spectrum of weeds, specifically including morning glories, and efficacy as sugarcane ripeners or harvest aids at application rates of less than half that of traditional chemical ripeners.

In accordance with the present invention, it has now been found that protoporphyrinogen oxidase enzyme-inhibiting (PPO-inhibiting) compounds are useful as chemical ripeners. Specifically, the present invention is a method for ripening sugarcane crops, which comprises applying an effective amount of one or more of a protoporphyrinogen oxidase enzyme-inhibiting compound, or an agriculturally-acceptable salt, ester, acid, or metabolite of such a compound to a crop where said ripening is desired. Other aspects of the present invention will become apparent from the description below.

DETAILED DESCRIPTION OF THE INVENTION

The present invention relates to a method for ripening sugarcane crops, which comprises applying an effective amount of a protoporphyrinogen oxidase enzyme-inhibiting compound, or an agriculturally-acceptable salt, ester, acid, or metabolite of such a compound to a crop where said ripening is desired. Another aspect of the present invention is a sugarcane harvest aid composition comprising a protoporphyrinogen oxidase enzyme-inhibiting compound in an amount sufficient to ripen the desired sugarcane crop.

As set forth above, compositions comprising PPO-inhibiting compounds, and their agriculturally-acceptable salts, esters, acids, and metabolites find utility as chemical ripeners of sugarcane crops when applied by the methods of the present invention to a crop where such ripening is desired. Examples of PPO-inhibiting compounds which may be used in the present invention include, without limitation, one or more of acifluorfen-sodium, aclonifen, bifenox, chlomethoxyfen, chlornitrofen, ethoxyfen-ethyl, fluorodifen, fluoroglycofen-ethyl, fluoronitrofen, fomesafen, furyloxyfen, halosafen, lactofen, nitrofen, nitrofluorfen, oxyfluorfen, cinidon-ethyl, flumiclorac-pentyl, flumioxazin, profluazol, pyrazogyl, oxadiargyl, oxadiazon, pentoxazone, fluazolate, pyraflufen-ethyl, benzfendizone, butafenacil, fluthiacet-methyl, thidiazimin, azafenidin, carfentrazone ethyl, sulfentrazone, flufenpyr-ethyl, as well as other PPO-inhibiting compounds, and their agriculturally-acceptable salts, esters, acids, and metabolites. A preferred PPO-inhibiting compound for use as a chemical ripener is carfentrazone ethyl and the metabolites of carfentrazone ethyl, namely, i) α,2-dichloro-5-[4-(difluoromethyl)-4,5-dihydro-3-methyl-5-oxo-1H-1,2,4-triazol-1-yl]-4-fluorobenzenepropanoic acid (chloropropanoic acid), ii) 2-chloro-5-[4-(difluoromethyl)-4,5-dihydro-3-methyl-5-oxo-1H-1,2,4-triazol-1-yl]-4-fluorobenzenepropenoic acid (cinnamic acid), iii) 2-chloro-5-[4-(difluoromethyl)-4,5-dihydro-3-methyl-5-oxo-1H-1,2,4-triazol-1-yl]-4-fluorobenzoic acid (benzoic acid), and iv) 2-chloro-5-[4-(difluoromethyl)-4,5-dihydro-3-methyl-5-oxo-1H-1,2,4-triazol-1-yl]-4-fluorobenzenepropanoic acid (propanoic acid). An even more preferred PPO-inhibiting compound for use as a chemical ripener is carfentrazone ethyl:

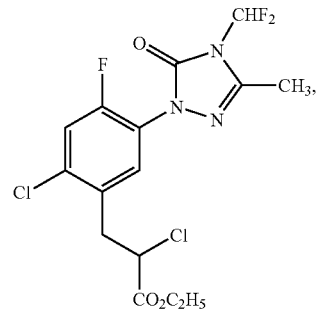

namely ethyl α,2-dichloro-5-[4-(difluoromethyl)-4,5-dihydro-3-methyl-5-oxo-1H-1,2,4-triazol-1-yl]-4-fluorobenzenepropanoate. Other analogs, homologs or derivatives of carfentrazone ethyl that may find utility in the methods of the present invention include the following:

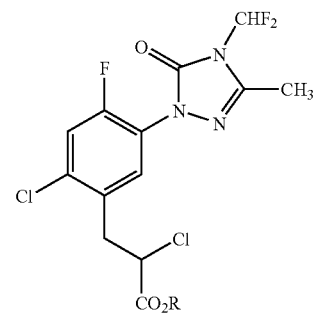

where R is selected from $CH_3$, $CH_2CH_2CH_3$, $CH(CH_3)_2$, $(CH_2)_3CH_3$, $CH_2CH(CH_3)_2$, n-pentyl, n-hexyl, $Na^+$, $K^+$, $Li^+$, $Ca^+$, and $NH_4^+$.

Carfentrazone ethyl, the metabolites, analogs, homologs or derivatives useful herein may be prepared by the methods taught in U.S. Pat. No. 5,125,958, the disclosure of which is incorporated herein by reference, or by methods analogous thereto, or by methods known to one skilled in the art.

Any amount of the PPO-inhibiting compound effective to achieve the desired ripening of the sugarcane may be employed. A preferred amount of the PPO-inhibiting compound is in the range of 40 grams ai/ha to 300 grams ai/ha. A preferred amount of carfentrazone ethyl is in the range of 60 grams ai/ha to 100 grams ai/ha.

Under certain conditions it may be advantageous in the ripening, of sugarcane crops to combine an effective amount of one or more of the PPO-inhibiting compounds of the present invention with a second chemical ripener. Of particular advantage is the combination with one or more other chemical ripeners for achieving the desired ripening effects on sugarcane crops, such as glyphosate and trinexapac-ethyl. A preferred combination of PPO-inhibiting compound and chemical ripeners for achieving the desired ripening effects on sugarcane crops is carfentrazone ethyl and one or more of glyphosate and trinexapac-ethyl.

Yet another embodiment of the present invention is the combination of a PPO-inhibitor compound with a second pesticide.

As used in this specification and unless otherwise indicated the terms "protoporphyrinogen oxidase enzyme-inhibiting", "protoporphyrinogen oxidase enzyme-inhibitor", "PPO-inhibiting", or "PPO-inhibitor" as these terms relate to the compounds of the present invention as set forth herein are one and the same. The term "chemical ripener" or "ripener" are defined as chemicals that artificially cause the ripening or enhance the natural ripening of a sugarcane crop. The term "ripening" is defined as an increase in sugar content in the sugarcane.

One skilled in the art will, of course, recognize that the formulation and mode of application of a ripener may affect the activity of the material in a given application. Thus, for use in the ripening of sugarcane crops, the PPO-inhibiting compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

The ripening compositions may be applied either as water-diluted sprays, dusts or granules to the crops in which ripening is desired. These formulations may contain as little as 0.1%, 0.2% or 0.5% to as much as 95% or more by weight of the PPO-inhibiting compound.

Dusts are free flowing admixtures of the PPO-inhibiting compound with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the ripening compound and 99.0 parts of talc.

Wettable powders are in the form of finely divided particles, which disperse readily in water or other dispersant. The wettable powder is ultimately applied either as a dry dust or as an emulsion in water or other liquid. Typical carriers for wettable powders include Fuller's earth, kaolin clays, silicas, and other highly absorbent, readily wet inorganic diluents.

Wettable powders normally are prepared to contain about 5-80% of PPO-inhibiting compound, depending on the absorbency of the carrier, and usually also contain a small amount of a wetting, dispersing or emulsifying agent to facilitate dispersion. For example, a useful wettable powder formulation contains 80.0 parts of the ripening compound, 17.9 parts of Palmetto clay, and 1.0 part of sodium lignosulfonate and 0.3 part of sulfonated aliphatic polyester as wetting agents.

Other useful formulations for these harvest aid applications are emulsifiable concentrates (ECs) which are homogeneous liquid compositions dispersible in water or other dispersant, and may consist entirely of the PPO-inhibiting compound and a liquid or solid emulsifying agent, or may also contain a liquid carrier, such as xylene, heavy aromatic naphthas, isphorone, or other non-volatile organic solvents. For harvest aid application these concentrates are dispersed in water or other liquid carrier and normally applied as a spray to the area to be treated. The percentage by weight of the PPO-inhibiting compound may vary according to the manner in which the composition is to be applied, but in general comprises 0.5 to 95% of the PPO-inhibiting compound by weight of the ripening composition.

Flowable formulations are similar to ECs except that the PPO-inhibiting compound is suspended in a liquid carrier, generally water. Flowables, like ECs, may include a small amount of a surfactant, and will typically contain PPO-inhibiting compounds in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in these formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long chain mercaptans and ethylene oxide. Many other types of useful surface-active agents are available in commerce. Surface-active agents, when used, normally comprise from 1 to 15% by weight of the composition.

Still other useful formulations for harvest aid applications include simple solutions of the PPO-inhibiting compound in a solvent in which it is completely soluble at the desired concentration, such as acetone, alkylated naphthalenes, xylene, or other organic solvents. Granular formulations, wherein the PPO-inhibiting compound is carried on relative coarse particles, are of particular utility for aerial distribution or for penetration of a cover canopy. Pressurized sprays, typically aerosols wherein the PPO-inhibiting compound is dispersed in finely divided form as a result of vaporization of a low-boiling dispersant solvent carrier may also be used. Water-soluble or water-dispersible granules are free-flowing, non-dusty, and readily water-soluble or water-miscible. In use in the field, the granular formulations, emulsifiable concentrates, flowable concentrates, solutions, etc., may be diluted with water to give a concentration of PPO-inhibiting compound in the range of from 0.1% or 0.2% to 1.5% or 2%.

The following example further illustrates the present invention, but, of course, should not be construed as in any way limiting its scope. The example includes a protocol for the evaluation of certain PPO-inhibiting compounds as ripeners on sugarcane crops, and sets forth certain data indicating the effectiveness of such compounds. Yield is measured in % POL, which is the percent saccharose content in the pressed broth or the cane. Purity and % BRIX (defined as total sugar content including glucose, fructose, saccharose and minerals) are also measures of crop yield, although the saccharose content is of primary concern.

EXAMPLE

Evaluation of Carfentrazone-Ethyl as a Sugarcane Ripener

The trial was performed on sugarcane, variety RB 81-5156 (plant-cane). The sugarcane was planted with spacing of 1.40 m between rows, using 30 kg/ha of N; 100 kg/ha of $P_2O_5$ and 80 gk/ha of $K_2O$ as basic fertilizers, complemented by a covering application of 30 kg/ha of N.

The application of ripeners was performed with pressurized back-pack sprayers, with flat fan nozzle 110.01. The flow was 65 l/ha and the pressure was 35 lb/in$^2$.

The experimental design used randomized plots with 6 treatments and 4 replications. The size of each experimental plot was 126 m$^2$ (6 spacing lines of 1.40 m per 15 m of length).

The climatic conditions at the time of the ripener applications were: average temperature of 27° C.; air relative humidity of 73%, wind speed of 4 km/hour.

One linear meter of stems was harvested in each experimental plot at 0 (zero), 15, 30 and 45 days after application (DAA) of the ripener. The sugar was extracted from these stems and submitted for GC and refractometer analysis of percent saccharose, glucose, fructose and minerals corresponding to % POL, % BRIX and % PURITY.

The results, shown as an average of four replications, were compared with results observed in the same trials with trinexapac-ethyl (Moddus). The results and comparison are in the tables below.

TABLE 1

% POL in Pressed Broth of Sugarcane Crop after Application of Ripeners

| Treatment | Rate (g ai/ha) | 0 DAA % POL | 15 DAA % POL | 30 DAA % POL | 45 DAA % POL |
|---|---|---|---|---|---|
| Carfentrazone-ethyl | 30 | 11.90 | 12.35 | 12.75 | 12.20 |
| Carfentrazone-ethyl | 40 | 12.55 | 13.18 | 13.70 | 13.58 |
| Carfentrazone-ethyl | 60 | 12.55 | 13.58 | 14.50 | 14.35 |
| Carfentrazone-ethyl | 80 | 12.45 | 14.08 | 15.05 | 15.30 |
| Carfentrazone-ethyl | 100 | 12.50 | 14.70 | 15.90 | 15.75 |
| trinexapac-ethyl | 250 | 12.75 | 14.25 | 15.80 | 15.75 |
| Check (untreated) | — | 12.18 | 11.98 | 12.25 | 12.55 |

% POL = 'saccharose'

TABLE 2

% POL in the Cane of Sugarcane Crop after Application of Ripeners

| Treatment | Rate (g ai/ha) | 0 DAA % POL | 15 DAA % POL | 30 DAA % POL | 45 DAA % POL |
|---|---|---|---|---|---|
| Carfentrazone-ethyl | 30 | 10.38 | 10.68 | 10.75 | 10.75 |
| Carfentrazone-ethyl | 40 | 10.38 | 10.63 | 10.98 | 11.00 |
| Carfentrazone-ethyl | 60 | 10.63 | 11.38 | 12.45 | 12.38 |
| Carfentrazone-ethyl | 80 | 10.80 | 11.93 | 13.25 | 13.35 |
| Carfentrazone-ethyl | 100 | 10.98 | 12.25 | 13.83 | 13.43 |
| trinexapac-ethyl | 250 | 11.35 | 12.53 | 13.45 | 14.20 |
| Check (untreated) | — | 10.30 | 10.55 | 10.45 | 10.50 |

% POL = 'saccharose'

TABLE 3

% PURITY in Pressed Broth of Sugarcane Crop after Application of Ripeners

| Treatment | Rate (g ai/ha) | 0 DAA % PURITY | 15 DAA % PURITY | 30 DAA % PURITY | 45 DAA % PURITY |
|---|---|---|---|---|---|
| Carfentrazone-ethyl | 30 | 78.48 | 79.10 | 79.50 | 79.35 |
| Carfentrazone-ethyl | 40 | 78.90 | 80.28 | 81.20 | 81.43 |
| Carfentrazone-ethyl | 60 | 79.35 | 81.85 | 83.15 | 83.15 |
| Carfentrazone-ethyl | 80 | 80.05 | 82.90 | 84.45 | 84.05 |
| Carfentrazone-ethyl | 100 | 81.85 | 83.78 | 86.05 | 83.38 |
| trinexapac-ethyl | 250 | 81.53 | 83.73 | 85.15 | 84.78 |
| Check (untreated) | — | 78.15 | 78.63 | 78.90 | 79.63 |

TABLE 4

% BRIX in Pressed Broth of Sugarcane Crop after Application of Ripeners

| Treatment | Rate (g ai/ha) | 0 DAA % BRIX | 15 DAA % BRIX | 30 DAA % BRIX | 45 DAA % BRIX |
|---|---|---|---|---|---|
| Carfentrazone-ethyl | 30 | 14.80 | 15.40 | 16.15 | 16.40 |
| Carfentrazone-ethyl | 40 | 14.50 | 15.50 | 16.98 | 16.90 |
| Carfentrazone-ethyl | 60 | 14.60 | 15.20 | 17.75 | 17.45 |
| Carfentrazone-ethyl | 80 | 14.50 | 15.80 | 17.90 | 17.80 |
| Carfentrazone-ethyl | 100 | 14.90 | 15.30 | 18.25 | 18.60 |
| trinexapac-ethyl | 250 | 14.93 | 15.15 | 17.85 | 18.45 |
| Check (untreated) | - | 14.48 | 15.25 | 17.28 | 18.45 |

% BRIX = 'glucose + fructose + saccharose + minerals'

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for increasing the sugar content in a sugarcane crop comprising applying an effective amount of a protoporphyrinogen oxidase enzyme-inhibiting compound to said crop in the middle or at the end of said crop's crop season, at least 15 days prior to harvest.

2. The method of claim 1, wherein said compound is selected from the group consisting of acifluorfen-sodium, aclonifen, bifenox, chlomethoxyfen, chlornitrofen, ethoxyfen-ethyl, fluorodifen, fluoroglycofen-ethyl, fluoronitrofen, fomesafen, furyloxyfen, halosafen, lactofen, nitrofen, nitrofluorfen, oxyfluorofen, cinidon-ethyl, flumiclorac-pentyl, flumioxazin, profluazol, pyrazogyl, oxadiargyl, oxadiazon, pentoxazone, fluazolate, pyraflufen-ethyl, benzfendizone, butafenacil, fluthiacet-methyl, thidiazimin, azafenidin, carfentrazone ethyl, sulfentrazone, flufenpyr-ethyl, and their agriculturally-acceptable salts, esters, acids, and metabolites.

3. The method of claim 2, wherein said compound is selected from the group consisting of carfentrazone ethyl and metabolites of carfentrazone ethyl.

4. The method of claim 3, wherein said metabolites are selected from the group consisting of i) α,2-dichloro-5-[4-(difluoromethyl)-4,5-dihydro-3-methyl-5-oxo-1H-1,2,4-triazol-1-yl]-4-fluorobenzenepropanoic acid, ii) 2-dichloro- 5-[4-(difluoromethyl)-4,5-dihydro-3-methyl-5-oxo-1H-1,2,4-triazol-1-yl]-4-fluorobenzenepropenoic acid, iii) 2-dichloro-5-[4-(difluoromethyl)-4,5-dihydro-3-methyl-5-oxo-1H-1,2,4-triazol-1-yl]-4-fluorobenzoic acid, and iv) 2-chloro-5-[4-(difluoromethyl)-4,5-dihydro-3-methyl-5-oxo-1H-1,2,4-triazol-1-yl]-4-fluorobenzenepropanoic acid.

5. The method of claim 3, wherein said compound is carfentrazone ethyl.

6. The method of claim 1, wherein the amount of said compound is in the range of 40 grams ai/ha to 300 grams ai/ha.

7. The method of claim 5, wherein the amount of said compound is in the range of 60 grams ai/ha to 100 grams ai/ha.

8. The method of claim 1, wherein said compound is combined with a second chemical ripener.

9. The method of claim 8, wherein said second chemical ripener is selected from the group consisting of glyphosate and trinexapac-ethyl.

10. The method of claim 9, wherein said compound is carfentrazone ethyl.

11. The method of claim 5 wherein the sugarcane crop has a percent saccharide content in the cane of at least 10.30% at the time of application.

* * * * *